United States Patent [19]

Starkey

[11] Patent Number: 5,528,369
[45] Date of Patent: Jun. 18, 1996

[54] APPARATUS FOR PRODUCING INTERFEROMETRIC FRINGE PATTERNS HAVING VARIABLE PARAMETERS

[75] Inventor: Douglas E. Starkey, Florissant, Mo.

[73] Assignee: American Cyanamid Company, Wayne, N.J.

[21] Appl. No.: 171,072

[22] Filed: Dec. 21, 1993

[51] Int. Cl.⁶ ........................................... G01B 9/02
[52] U.S. Cl. ..................... 356/351; 356/345; 356/353
[58] Field of Search ........................... 356/351, 345, 356/359, 360, 35.5, 374, 353, 354

[56] References Cited

U.S. PATENT DOCUMENTS

| | | | |
|---|---|---|---|
| 3,517,982 | 6/1970 | Fonda-Bonardi | 356/345 |
| 4,009,940 | 3/1977 | Ohzu | 356/354 |
| 4,991,963 | 2/1991 | Sutton | 356/353 |
| 5,176,147 | 1/1993 | Bodis-Wollner | 128/745 |
| 5,216,458 | 6/1993 | Andera et al. | 351/243 |
| 5,223,865 | 6/1993 | Shirao et al. | 351/243 |

FOREIGN PATENT DOCUMENTS 3245006  10/1991  Japan ................................ 356/351

*Primary Examiner*—Samuel A. Turner
*Attorney, Agent, or Firm*—Montgomery W. Smith; Brian R. Woodworth; Ari M. Bai

[57] ABSTRACT

An apparatus for producing a fringe pattern having variable parameters. The apparatus includes a light source which directs light to a first beamsplitter which transmits a first portion of the light beam along a first light path and reflects a second portion of the light beam along a second light path. The apparatus is further configured to cause the first and second light paths to converge at a second beamsplitter. A half-wave retarder is provided along the first light path in order to rotate the plane of polarization of the light traveling along the first light path by approximately 90° such that the light traveling along the first and second light paths creates a fringe pattern upon convergence at the second beamsplitter. The apparatus is further configured such that one or more of the contrast, temporal frequency, spatial frequency, and orientation of the fringe pattern can be selectively varied.

20 Claims, 2 Drawing Sheets

APPARATUS FOR PRODUCING INTERFEROMETRIC FRINGE PATTERNS HAVING VARIABLE PARAMETERS

BACKGROUND OF THE INVENTION

The present invention relates to an apparatus for producing interferometric fringe patterns. In particular, the present invention is directed to an apparatus for producing interferometric fringe patterns such that the contrast, spatial frequency, temporal frequency, intensity, and orientation of the interferometric fringe pattern can be selectively varied.

The production of interferometric fringe patterns is relatively well-known. For example, interferometric fringe patterns produced by shearing interferometers and other known devices are used in a variety of applications, including pattern electroretinogram testing, as disclosed and claimed in U.S. Pat. No. 5,233,373 to Peters, et al. issued Aug. 3, 1993. Interferometric fringe patterns can also be used in conjunction with visual acuity and contrast sensitivity testing, as disclosed in U.S. Pat. No. 5,216,458 to Andera, et al. issued Jun. 1, 1993.

Known devices and methods for producing fringe patterns typically employ polychromatic illumination of diffraction gratings, Moire fringes, or shearing interferometry to produce the desired fringes. However, such known devices and methods have inherent limitations in their application due to the limited number of parameters which can be varied as well as the limited range and resolution over which these parameters can be varied.

For example, the device disclosed in U.S. Pat. No. 5,216,458 to Andera, et al. generates a variable contrast and spatial frequency fringe pattern to the eye for the purpose of measuring visual acuity and contrast sensitivity. However, the number of spatial frequencies that can be tested using a device of this type is limited by the number of spatial frequency "optotypes". In addition, the device provides no mechanism for the variation of the temporal frequency or the orientation of the fringe pattern. Furthermore, the device disclosed by Andera, et al. does not use a monochromatic light source and is thus susceptible to test errors caused by ocular chromatic aberrations.

Known devices and methods for producing fringe patterns are typically inefficient with respect to light transmission. For example, a shearing interferometer typically loses approximately 90%–95% of the intensity of the source light when used to create interferometric fringe patterns. Due to this relatively inefficient use of the source light, a relatively high-powered light source is required in order to generate a viable fringe pattern. The need for a higher powered light source increases the power requirements of the apparatus as well as increasing the space occupied by the device.

SUMMARY OF THE INVENTION

The present invention is directed to an apparatus for producing interferometric fringe patterns. The apparatus includes a light source and a linear polarizer for polarizing the light emitted from the light source. The polarized light is directed to a polarizing beamsplitter having a capacity to divide the incident light beam into two distinct, orthogonally polarized light paths. The first light path produced by the polarizing beamsplitter passes through a half-wave retarder which rotates the plane of polarization of the light passing therethrough by 90°, thereby polarizing the light traveling along the first and second light paths in the same plane. The apparatus is further configured such that the first and second light paths converge at a non-polarizing beamsplitter. Due to the fact that the first and second light paths are polarized in the same plane, the recombination of light traveling along the first and second light paths produces a fringe pattern which can be used in conjunction with any apparatus requiring a fringe pattern.

In an alternative embodiment of the invention, the apparatus further includes a dither plate placed in either the first light path or the second light path in order to vary the optical path length thereof. The temporal frequency of the fringe pattern thus can be varied by selectively positioning the dither plate. In another embodiment of the present invention, the apparatus further includes a first movable mirror disposed in either the first or second light path, the mirror being movable such that the spatial frequency of the resulting interference pattern can be varied by moving the mirror in a predetermined direction. The apparatus can further include a second mirror disposed in the first or second light path, the mirror being movable such that the physical orientation of the fringe pattern produced by the apparatus can be varied by selectively positioning the second mirror. Additional alternative embodiments of the present invention are described and claimed herein.

BRIEF DESCRIPTION OF THE DRAWINGS

For a more complete understanding of the present invention, reference may be had to the following Detailed Description read in connection with the accompanying drawings in which.

DETAILED DESCRIPTION

Figure 1:
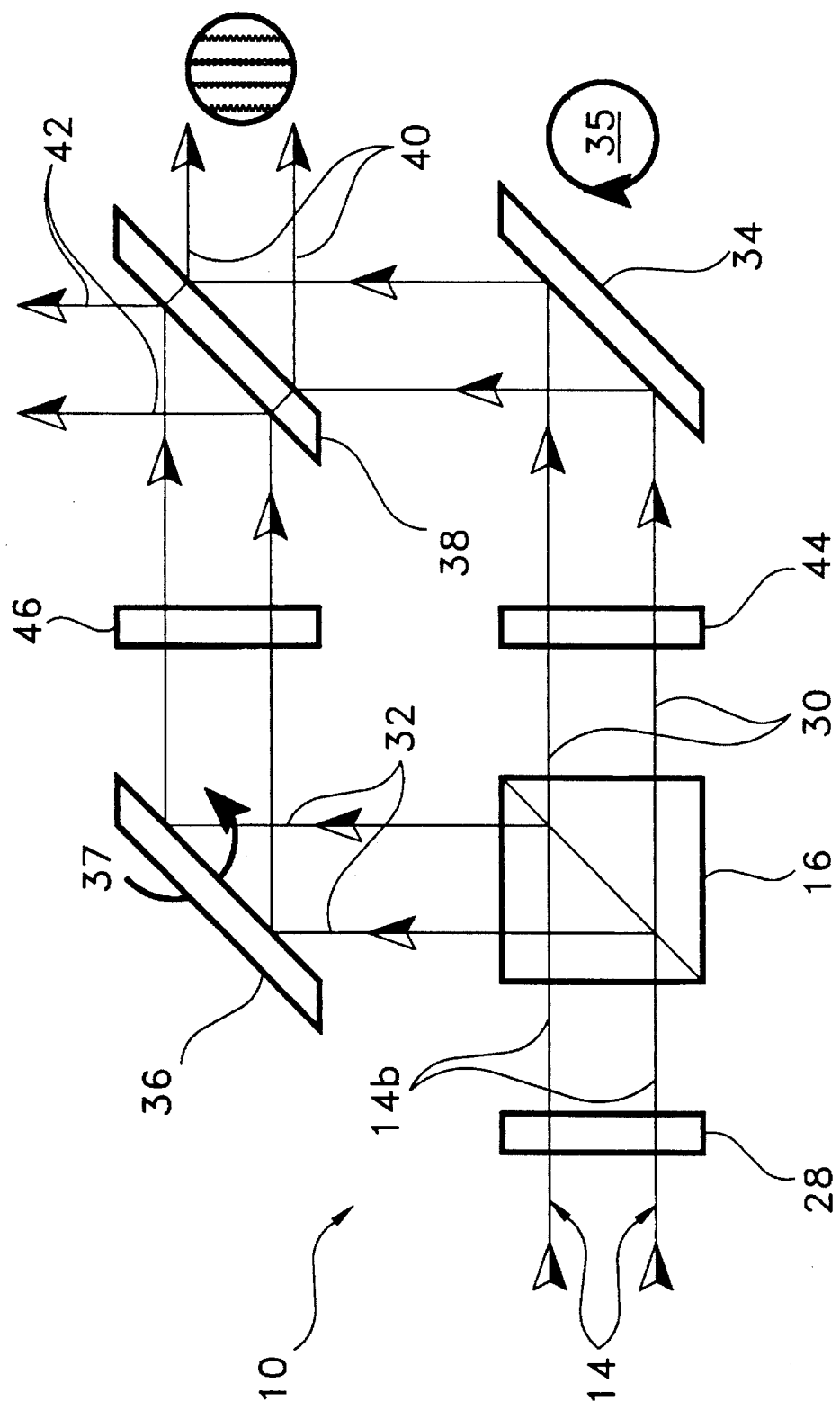
FIG. 1 is a schematic view of an apparatus constructed in accordance with the present invention.
Figure 2:
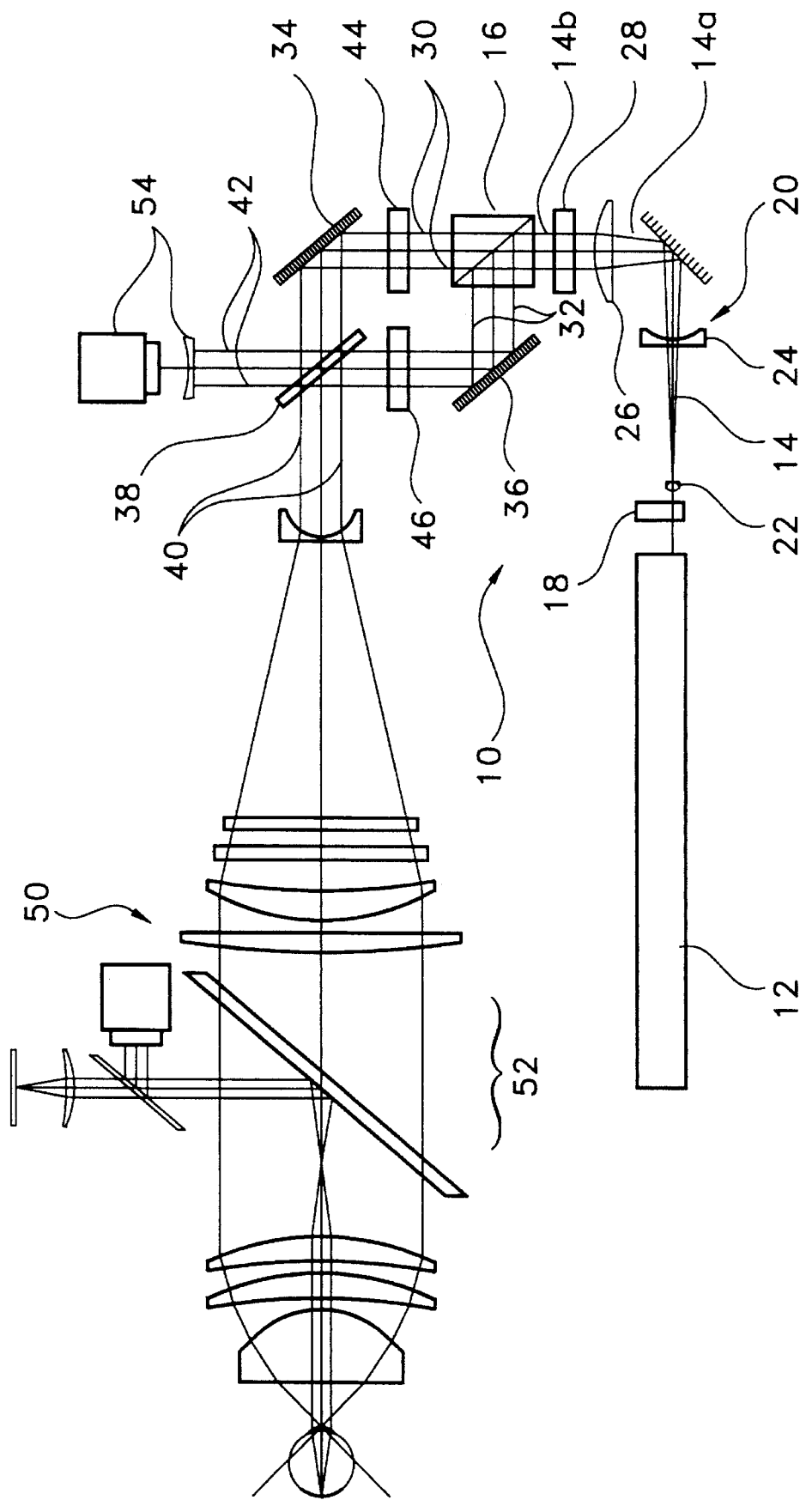
FIG. 2 is a schematic view of a first alternative embodiment of an apparatus constructed in accordance with the present invention in combination with a device used in conjunction with pattern electroretinogram testing.

An apparatus for generating fringe patterns constructed in accordance with the present invention is generally indicated at 10 of FIGS. 1 and 2. The apparatus includes light source 12 which directs incident light beam 14 to first beamsplitter 16. Light source 12 preferably provides a spatially and temporally coherent light beam for use in connection with the present invention. Light source 12 also preferably provides a monochromatic light beam in order to prevent testing errors arising from ocular chromatic aberrations when apparatus 10 is used in conjunction with an ocular testing device. It has been found that many laser light sources provide the desired characteristics. However, it will be appreciated that a variety of other known light sources can be used without departing from the spirit and scope of the present invention.

In the embodiment of the present invention depicted in FIG. 2, intensity control 18 is disposed between light source 12 and first beamsplitter 16 in order to allow the intensity of incident light beam 14 to be varied. Intensity control 18, as depicted in FIG. 2, is a circular variable neutral density wheel of known construction. A circular variable neutral density wheel is constructed such that distinct portions thereof attenuate different percentages of light passing therethrough. Thus, the intensity of incident light beam 14 can be selectively altered simply by rotating the circular variable neutral density wheel to a selected position. The rotation of the circular variable neutral density wheel can be effected manually, mechanically, or electromechanically using known techniques and devices. It will be apparent to one of ordinary skill in the art that other known mechanisms can be used in order to vary the intensity of incident light beam 14.

The alternative embodiment of the present invention depicted in FIG. 2 further includes beam expander 20 disposed between light source 12 and first beamsplitter 16. It will be appreciated that beam expander 20 should be used in those cases in which a laser is used as light source 12 due to the fact lasers typically emit a beam of light having a diameter of less than 1 mm. Thus, it is necessary to expand the light beam in order to produce the desired fringe pattern. Beam expander 20 provides this capacity. In a preferred embodiment of the present invention, beam expander 20 preferably has a capacity to expand incident light beam 14 up to a diameter of at least 20 mm.

Various methods for expanding a beam of light can be used in conjunction with the present invention. In the embodiment depicted in FIG. 2, beam expander 20 includes achromat 22 which focuses incident light beam 14. The focused incident light beam 14 is then directed through plano-concave lens 24 which causes incident light beam 14 to diverge, thereby forming a broadened incident light beam 14a.

Beam expander 20, as depicted in FIG. 2 can further include plano-convex lens 26 which causes broadened light beam 14a to be refracted such that the light in incident light beam 14 is substantially collimated after passing therethrough.

Linear polarizer 28 is positioned such that incident light beam 14 passes therethrough prior to reaching first beamsplitter 16. Linear polarizer 28 polarizes the light of incident light beam 14 to produce a polarized light beam 14b. Linear polarizer 28 preferably has a capacity to provide for the selective variation of the plane of polarization of the polarized light beam transmitted therefrom. As discussed in detail below, the contrast of the fringe pattern produced by apparatus 10 preferably can be varied from approximately 0% to 100% by varying the plane of polarization of the polarized light beam using linear polarizer 28. Linear polarizers having the characteristics of linear polarizer 28 described herein are known in the art.

First beamsplitter 16 has a capacity to split incident light beam 14 into first light path 30 and second light path 32. First beamsplitter 16 also preferably has a polarizing capacity such that light traveling along first light path 30 and second light path 32 is polarized in first and second orthogonal planes of polarization, respectively. Beamsplitters having the desired characteristics of first beamsplitter 16 are known in the art. It will be appreciated by one of ordinary skill in the art that the first and second planes of polarization typically will be oriented at approximately 90° relative to one another due to the optical characteristics of first beamsplitter 16.

By selectively varying the orientation of linear polarizer 28, the polarization axis of incident light path 14 is rotated relative to the polarization of first beamsplitter 16, thereby effecting a variation in the intensities of light in first light path 30 and second light path 32 in order to alter the contrast of the fringe pattern produced by apparatus 10. As above-discussed, it is preferable that linear polarizer 28 and first beamsplitter 16 be relatively configured such that it is possible to vary the contrast of the fringe pattern produced by apparatus 10 from approximately 0% to 100% by rotating linear polarizer 28.

In the embodiment of the present invention depicted in FIGS. 1 and 2, first flat mirror 34 is positioned along first light path 30. First flat mirror 34 is positioned such that first light path 30 converges upon second light path 32 following reflection from first flat mirror 34. Second light path 32 includes second flat mirror 36 which reflects light traveling along second light path 32 such that second light path 32 converges upon and crosses first light path 30 as depicted in FIGS. 1 and 2.

It is preferable that one or both of first flat mirror 34 and second flat mirror 36 be movable in order to vary the spatial frequency and/or orientation of the fringe pattern produced using apparatus 10. As depicted in FIG. 1, first flat mirror 34 is preferably mounted such that it is pivotable in a direction represented by arrow 35 about an axis perpendicular to the direction of first light path 30, i.e., such that first flat mirror 34 rotates in the plane of the page on which FIG. 1 is depicted. Rotation of first flat mirror 34 in this plane will cause the orientation of the fringe pattern produced by apparatus 10 to rotate, as will be appreciated by those of ordinary skill in the art. It will also be appreciated that apparatus 10 of the present invention can be configured such that second flat mirror 36 is movable in the same above-described plane in order to effect the same type of change to the orientation of the fringe pattern produced by apparatus 10 of the present invention.

Second flat mirror 36 is preferably mounted such that it is pivotable in a direction indicated by arrow 37 about an axis perpendicular to the direction of second light path 32 and perpendicular to the axis of rotation of first flat mirror 34, i.e., such that second flat mirror 36 is pivotable out of the plane of the page on which FIG. 1 is depicted. Movement of second flat mirror 36 will cause the spatial frequency of the fringe pattern produced by apparatus 10, i.e., the number of dark/light bands per a see unit of length, to vary. Here again, it will be appreciated that first flat mirror 34 can be configured to move in the same plane in order to effect the same type of change to the spatial frequency of the fringe pattern produced by apparatus 10 of the present invention using externally-mounted controls or remote controls of known construction.

Rotation of first and second flat mirrors 34, 36 can be effected manually, or can be achieved through a variety of known mechanical and electromechanical methods which do not form a part of the present invention. However, it is preferable that rotation be effected mechanically or electromechanically in a controlled manner such that a person operating apparatus 10 can readily alter the respective orientations of first and second flat mirrors 34, 36.

Second beamsplitter 38 is positioned such that first light path 30 and second light path 32 converge at second beamsplitter 38, as depicted in FIGS. 1 and 2. Second beamsplitter 38 preferably is non-polarizing and thus does not substantially alter the orientation of light passing therethrough. Second beamsplitter 38 directs the combined light from first light path 30 and second light path 32 along first outgoing light path 40 and second outgoing light path 42. The recombination of light from first and second light paths 30, 32 produces a fringe pattern which is directed along both first and second outgoing light paths 40, 42, as discussed in greater detail below. The respective intensities of light passing along first and second outgoing paths 40, 42 can be varied by changing the coating characteristics of second beamsplitter 38. The optical characteristics of second beamsplitter 38 should be selected based upon the particular circumstances under which apparatus 10 of the present invention is to be used. For example, in one embodiment of the present invention, second plate beamsplitter 38 is constructed such that the intensities of first and second outgoing paths 40, 42 are approximately equal.

Half-wave retarder 44 can be positioned along first light path 30 between first beamsplitter 16 and first flat mirror 34 as depicted in FIGS. 1 and 2. However, half-wave retarder 44 also can be positioned at any point along second light path 32 between first beamsplitter 16 and second beamsplitter 38. Half-wave retarder 44, when oriented with its fast-axis at 45° relative to the plane of polarization of light in light path 30, causes the plane of polarization of light in light path 30 to rotate by approximately 90° upon transmission. Due to the fact that first beamsplitter 16 causes the light in light paths 30, 32 to be polarized in orthogonal planes, as above-discussed, half-wave retarder 44 thus has the capacity to reorient light traveling along first light path 30 such that the planes of polarization of light in light paths 30, 32 are aligned substantially in the same plane at the time that they reach second beamsplitter 38. Thus, when first and second light paths 30, 32 converge and recombine at second beamsplitter 38, a fringe pattern is produced.

In the embodiment of the invention depicted in FIG. 2, dither plate 46 is mounted such that light traveling along second light path 32 passes therethrough. It will be appreciated that dither plate 46 can also be positioned along first light path 30 and perform the same function described herein. Dither plate 46 preferably is preferably of known configuration and is constructed of glass. Dither plate 46 provides control over the relative optical path length traversed by first and second light paths 30, 32, and thereby allows the temporal frequency of the fringe pattern produced by apparatus 10, i.e., the rate at which the fringe pattern bands shift from dark to light, to be varied by moving or oscillating dither plate 46 at selectively varying rates. Dither plate 46 can be moved to different positions in order to provide a predetermined path difference between first and second light paths 30, 32.

In the embodiment of the present invention depicted in FIG. 2, dither plate 46 is mounted such that it can be oscillated between two positions. In a preferred embodiment of the present invention, the two positions of dither plate 46 provide an optical path difference of one-half wavelength per oscillation, thereby reversing the light and dark bands of the fringe pattern created by apparatus 10. Oscillation of dither plate 46 can be performed manually, but preferably is performed through known mechanical or electromechanical methods. Dither plate 46, and the electromechanical or mechanical methods by which it is oscillated, are preferably constructed and disposed within apparatus 10 such that the temporal frequency of the fringe pattern produced by apparatus 10 can be selectively controlled by an individual operating apparatus 10 by selectively controlling the oscillation of dither plate 46.

As above-discussed, first and second outgoing paths 40, 42 contain a fringe pattern due to interference between light traveling along first and second light paths 30, 32. In the embodiment of the present invention depicted FIG. 2, the intensity of light in the fringe pattern can be varied by selectively varying intensity control 18, i.e., by selectively varying the orientation of the circular variable neutral density wheel used as an intensity control. In addition, the contrast of the fringe pattern produced by apparatus 10 can be varied by selectively changing the orientation of linear polarizer 28, as above-discussed. Further, the spatial frequency of the fringe pattern produced by apparatus 10 can be varied by selectively changing the position of first or second flat mirror 34, 36 about a first axis of rotation. The orientation of the fringe pattern produced by apparatus 10 can be varied by selectively changing the position of first or second flat mirror 34, 36 about a second axis of rotation, the second axis being perpendicular to the first axis. Finally, the temporal frequency of the fringe pattern produced by apparatus 10 can be varied through the selective oscillation of dither plate 46. Thus, apparatus 10 produces a variable fringe pattern with a minimal number of elements. In addition, apparatus 10 requires less light than a conventional shearing interferometer due to the fact that apparatus 10 maintains five to ten times more of the intensity of the light source when compared to a shearing interferometer.

In the alternative embodiment depicted in FIG. 2, apparatus 10 of the present invention is shown in combination with a system for pattern electroretinogram ("PERG") testing which is generally identified at 50 in FIG. 2. PERG system 50 includes an optical system 52 constructed to project the fringe pattern produced by apparatus 10 such that it converges in order to pass through the pupil and then diverges such that the fringe pattern is projected on the retina, thereby facilitating diagnostic testing of a substantial portion of the retina. In this embodiment, second outgoing path 42 is directed to optical feedback monitor 54. For a better understanding of the purpose and function of PERG system 50, reference should be made to U.S. Pat. No. 5,233,373 to Peters, et al. issued Aug. 3, 1993 which is incorporated herein by reference.

Although the apparatus of the present invention has been disclosed herein with respect to certain preferred embodiments, it will be apparent to one of ordinary skill in the art that various modifications can be made to the apparatus without departing from the spirit and scope of the invention disclosed and claimed herein.

What is claimed is:

1. An apparatus for producing a fringe pattern, said apparatus comprising:

a light source, said light source having a capacity to generate an incident light beam;

a polarizer positioned such that said incident light beam passes therethrough to form a polarized light beam, said polarizer having a capacity selectively to rotate a plane of polarization of said polarized light beam;

a first beamsplitter disposed such that a first portion of said polarized light beam is transmitted therethrough along a first light path and such that a second portion of said polarized light beam is reflected thereby along a second light path, said first beamsplitter being positioned distal to said light source relative to said polarizer, said first beamsplitter having a capacity to polarize said first portion of said polarized light beam and said second portion of said polarized light beam in first and second planes of polarization, said first and second planes of polarization being orthogonal to one another, whereby a contrast of said fringe pattern produced by said apparatus can be varied by selectively rotating said plane of polarization of said polarized light beam using said polarizer;

a half-wave retarder positioned along said first light path such that said first portion of said polarized light beam passes therethrough, said half-wave retarder having a capacity to rotate said first plane of polarization of said first portion of said polarized light beam by approximately 90°, whereby said second portion of said polarized light beam and said first portion of said polarized light beam are polarized in the same plane after said first portion of said polarized light beam passes through said half-wave retarder; and a second beamsplitter disposed at a point where said first light path and said second light path converge, said second beamsplitter having a capacity to transmit a first outgoing light path containing said fringe pattern.

2. An apparatus for producing a fringe pattern in accordance with claim 1, wherein said second beamsplitter has a capacity to transmit a second outgoing light path containing said fringe pattern.

3. An apparatus for producing a fringe pattern in accordance with claim 1, wherein said apparatus further comprises a dither plate positioned along said second light path such that said second portion of said polarized light beam passes therethrough, said dither plate having a capacity to control an optical path length of said second light path and thereby having a capacity to vary a temporal frequency of said fringe pattern produced by said apparatus.

4. An apparatus for producing a fringe pattern in accordance with claim 3, wherein said dither plate is pivotably mounted along said second light path whereby said dither plate can be oscillated between a first position and a second position in order to vary said temporal frequency of said fringe pattern, and whereby oscillation of said dither plate between said first and said second positions varies said optical path length of said second light path by approximately one-half of a wavelength of said incident light beam.

5. An apparatus for producing a fringe pattern in accordance with claim 1, wherein said apparatus further comprises a dither plate positioned along said first light path such that said first portion of said polarized light beam passes therethrough, said dither plate having a capacity to control an optical path length of said first light path and thereby having a capacity to vary a temporal frequency of said fringe pattern produced by said apparatus.

6. An apparatus for producing a fringe pattern in accordance with claim 5, wherein said dither plate is pivotably mounted along said first light path whereby said dither plate can be oscillated between a first position and a second position in order to vary said temporal frequency of said fringe pattern, and whereby oscillation of said dither plate between said first and said second positions varies said optical path length of said second light path by approximately one-half of a wavelength of said incident light beam.

7. An apparatus for producing a fringe pattern in accordance with claim 1, wherein said apparatus further comprises a first mirror positioned along said first light path such that said first portion of said polarized light beam is reflected thereby toward said second beamsplitter.

8. An apparatus for producing a fringe pattern in accordance with claim 7, wherein said first mirror is pivotable about a first axis perpendicular to a direction of said first light path, whereby a spatial frequency of said fringe pattern can be varied by selectively positioning said first mirror about said first axis.

9. An apparatus for producing a fringe pattern in accordance with claim 7, wherein said first mirror is pivotable about a second axis perpendicular to a direction of said first light path, whereby an orientation of said fringe pattern can be varied by selectively positioning said first mirror about said second axis.

10. An apparatus for producing a fringe pattern in accordance with claim 1, wherein said apparatus further comprises a second mirror disposed along said second light path such that said second portion of said polarized light beam is reflected thereby toward said second beamsplitter.

11. An apparatus for producing a fringe pattern in accordance with claim 10, wherein said second mirror is pivotable about a first axis perpendicular to a direction of said second light path, whereby an orientation of said fringe pattern can be varied by selectively positioning said second mirror about said first axis.

12. An apparatus for producing a fringe pattern in accordance with claim 10, wherein said second mirror is pivotable about a second axis perpendicular to a direction of said second light path, whereby a spatial frequency of said fringe pattern can be varied by selectively positioning said second mirror about said second axis.

13. An apparatus for producing a fringe pattern in accordance with claim 1, wherein said light source is a laser, and wherein said apparatus further comprises a beam expander positioned between said light source and said polarizer, said beam expander having a capacity to broaden a diameter of said incident light beam produced by said laser.

14. An apparatus for producing a fringe pattern in accordance with claim 13, wherein said beam expander comprises a plano-concave lens, an achromat, and a plano-convex lens.

15. An apparatus for producing a fringe pattern, said apparatus comprising:

a light source, said light source having a capacity to generate an incident light beam;

a polarizer positioned such that said incident light beam passes therethrough to form a polarized light beam, said polarizer having a capacity selectively to rotate a plane of polarization of said polarized light beam;

a first beamsplitter disposed such that a first portion of said polarized light beam is transmitted therethrough along a first light path and such that a second portion of said polarized light beam is reflected thereby along a second light path, said first beamsplitter being positioned distal to said light source relative to said polarizer, said first beamsplitter having a capacity to polarize said first portion of said polarized light beam and said second portion of said polarized light beam in first and second planes of polarization, said first and second planes of polarization being orthogonal to one another, whereby a contrast of said fringe pattern produced by said apparatus can be varied by selectively rotating said plane of polarization of said polarized light beam using said polarizer;

a half-wave retarder positioned along said first light path such that said first portion of said polarized light beam passes therethrough, said half-wave retarder having a capacity to rotate said first plane of polarization of said first portion of said polarized light beam by approximately 90°, whereby said second portion of said polarized light beam and said first portion of said polarized light beam are polarized in a single plane after said first portion of said polarized light beam passes through said half-wave retarder;

a dither plate positioned along said second light path such that said second portion of said polarized light beam passes therethrough, said dither plate having a capacity to control an optical path length of said second light path and thereby having a capacity to vary a temporal frequency of said fringe pattern;

a second beamsplitter having a capacity to transmit a first outgoing light path containing said fringe pattern;

a first mirror positioned along said first light path such that said first portion of said polarized light beam is reflected thereby toward said second beamsplitter; and a second mirror disposed along said second light path such that said second portion of said polarized light beam is reflected thereby toward said second beamsplitter, whereby said first portion and said second portion of said polarized light beam converge at said second beamsplitter to form said fringe pattern.

16. An apparatus for producing a fringe pattern in accordance with claim 15, wherein said dither plate is pivotable between a first position and a second position, and whereby oscillation of said dither plate between said first and said second position varies said optical path length of said second light path by approximately one-half of a wavelength of said incident light beam.

17. An apparatus for producing a fringe pattern in accordance with claim 15, wherein said first mirror is pivotable about a first axis perpendicular to a direction of said first light path, whereby a spatial frequency of said fringe pattern can be varied by selectively positioning said first mirror about said first axis.

18. An apparatus for producing a fringe pattern in accordance with claim 15, wherein said second mirror is pivotable about a second axis perpendicular to a direction of said second light path, whereby an orientation of said fringe pattern can be varied by selectively positioning said second mirror about said second axis.

19. An apparatus for producing a fringe pattern in accordance with claim 18, wherein said first mirror is pivotable about a first axis perpendicular to a direction of said first light path and perpendicular to said second axis, whereby a spatial frequency of said fringe pattern can be varied by selectively positioning said first mirror about said first axis.

20. An apparatus for producing a fringe pattern, said apparatus comprising:

a light source, said light source having a capacity to generate an incident light beam;

a polarizer positioned such that said incident light beam passes therethrough to form a polarized light beam, said polarizer having a capacity selectively to rotate a plane of polarization of said polarized light beam;

a first beamsplitter disposed such that a first portion of said polarized light beam is transmitted therethrough along a first light path and such that a second portion of said polarized light beam is reflected thereby along a second light path, said first beamsplitter being positioned distal to said light source relative to said polarizer, said first beamsplitter having a capacity to polarize said first portion of said polarized light beam and said second portion of said polarized light beam in first and second planes of polarization, said first and second planes of polarization being orthogonal to one another, whereby a contrast of said fringe pattern produced by said apparatus can be varied by selectively rotating said plane of polarization of said polarized light beam using said polarizer;

a half-wave retarder positioned along said first light path such that said first portion of said polarized light beam passes therethrough, said half-wave retarder having a capacity to rotate said first plane of polarization of said first portion of said polarized light beam by approximately 90°, whereby said second portion of said polarized light beam and said first portion of said polarized light beam are polarized in a single plane after said first portion of said polarized light beam passes through said half-wave retarder;

a dither plate positioned along said second light path such that said second portion of said polarized light beam passes therethrough, said dither plate having a capacity to control an optical path length of said second light path and thereby having a capacity to vary a temporal frequency of said fringe pattern, said dither plate being pivotable between a first position, whereby oscillation of said dither plate between said first position and said second position varies said optical path length of said second light path by approximately one-half of a wavelength of said incident light beam;

a second beamsplitter having a capacity to transmit a first outgoing light path containing said fringe pattern;

a first mirror positioned along said first light path such that said first portion of said polarized light beam is reflected thereby toward said second beamsplitter, said first mirror being pivotable about a first axis perpendicular to a direction of said first light path, whereby a spatial frequency of said fringe pattern can be varied by selectively positioning said first mirror about said first axis; and a second mirror disposed along said second light path such that said second portion of said polarized light beam is reflected thereby toward said second beamsplitter, said second mirror being pivotable about a second axis perpendicular to a direction of said second light path and perpendicular to said first axis, whereby an orientation of said fringe pattern can be varied by selectively positioning said second mirror about said second axis, and whereby said first portion and said second portion of said polarized light beam converge at said second beamsplitter to form said fringe pattern.

* * * * *